United States Patent [19]

Lundgren et al.

[11] Patent Number: 4,756,689
[45] Date of Patent: Jul. 12, 1988

[54] CONNECTING DEVICES

[76] Inventors: Dan Lundgren, Kyrkvägen 5, S-430 80 Hovåas; Izidor Brajnovi, Narvavägen 10C, S-552 59 Jönköping, both of Sweden

[21] Appl. No.: 907,906

[22] Filed: Sep. 16, 1986

[30] Foreign Application Priority Data

Sep. 16, 1985 [SE] Sweden .................................. 8504274

[51] Int. Cl.⁴ ................................................ A61C 8/00
[52] U.S. Cl. ...................................... 433/173; 433/169
[58] Field of Search ............... 433/168, 169, 173, 174, 433/175, 176

[56] References Cited

U.S. PATENT DOCUMENTS

| | | | |
|---|---|---|---|
| 4,215,986 | 8/1980 | Riess et al. | 433/169 |
| 4,318,696 | 3/1982 | Kasama et al. | 433/169 |
| 4,324,550 | 4/1982 | Reuther et al. | 433/169 |
| 4,626,214 | 12/1986 | Artal | 433/169 |

Primary Examiner—Robert Peshock
Attorney, Agent, or Firm—Pollock, Vande Sande & Priddy

[57] ABSTRACT

A connecting device for oral and extra-oral prostheses which is partially implanted in bodily tissue, primarily bone tissue, by means of an anchorage unit (a fixture) that provides more favorable stress and force distribution between the implanted and the outer portion of the prosthesis located peri-tissually. The connecting device includes a cap-shaped matrix (6) whose base is connectable to the anchorage unit by an intermediary spacer (1), and the matrix (6) which includes a resilient portion, for example a separate O-ring member (9) by which the matrix is connected to the prosthesis outer portion (15), preferably through an outer sleeve-shaped patrix (11) so that this will become elastically anchored to the matrix (6).

11 Claims, 4 Drawing Sheets

CONNECTING DEVICES

TECHNICAL FIELD

The present invention relates to a connecting device included in oral and extra-oral prostheses of the type which is partially implanted in body tissue, primarily in bone tissue, by means of a particularly designed anchorage unit (a fixture). The intention is to provide by means of this connecting device, a more favorable stress and force distribution between the implanted and peri-tissual located portion of the prosthesis.

BACKGROUND ART

It is previously known in this Art to permanently anchor dental prostheses in the jawbone tissue. The method which has proved to result in the greatest anchorage stability—and the only method which has proved to afford a truly permanent anchorage in the bone tissue—is the so-called osseointegration method, developed by Professor Per-Ingvar Brånemark et. al. in Gothenburg, Sweden. The unique feature of this method is that the anchorage unit (the fixture) may be implanted, both very accurately and atraumatically, directly in the bone tissue without the necessity of interposed bonding tissue. This direct contact between fixture and bone tissue makes for optimum conditions for lasting heating by osseointegration.

The anchorage unit (the fixture) is in the form of a screw, preferably of titanium, and is implanted such that the upper portion of the screw is located flush with or slightly beneath the surface of the jawbone. This first operation is followed by a dentally unloaded healing period of a critical length, during which the screw is covered by intact mucosa. During this healing phase, the bone tissue grows onto and forms a unit with the implanted fixture. In the subsequent operation, the fixture is exposed and a spacer, also preferably made of titanium, is disposed on the fixture by means of a spacer screw. The dental prosthesis in the form of a crown or bridge construction, is then anchored in place by means of a locking screw which positionally fixes the spacer screw. This method has been successfully employed clinically for 20 years in conjunction with jawbone-anchored bridge constructions, and development is now underway concerning the anchorage of prostheses to other parts of the skeleton (extra-oral prostheses).

The unique properties of this method thus derive from the fact that the fixture is wholly incorporated in the bone tissue. This implies that the dental prosthesis will be relatively rigidly anchored in the jawbone, as opposed to, for example, the nature tooth which is more elastically supported. Such a rigid anchorage entails that the oral functional stresses are transmitted without attenuation to the dental prosthesis (the crown or bridge construction) and its anchorage (the spacer and the fixture), which may give rise to excessively high stresses in both the bone tissue anchorage and in the different components of the dental prosthesis. Even if the osseointegration method possesses uniquely advantageous properties as regards the risk of disengagement arising out of overloading, it is, of course nevertheless desirable to reduce, as far as is possible, the levels of force stresses. As a result, fracture of the prosthesis components can be avoided, at the same time as these may be dimensioned in such a manner as requires as little space as possible.

Concerning the oral functional and mastication forces, the velocity of forces and the mass involved are so insignificant that the damping effect of the elastic suspension on transmission of energy per unit of time should be of but marginal importance. Of considerably greater importance is the deflection which may be realized by elastic suspension of one or more, (individual or interconnected), jawbone-anchored crowns in residual bite with natural teeth. Depending upon the degree of elasticity and, thereby, deflection, the occlusal forces can be distributed between the jawbone-anchored units and the natural teeth in a controllable manner. A harmonically adapted degree of elasticity might well also contribute to an optimum level of oral comfort for the patient.

Not least in those cases where one or more jawbone-anchored units are connected to the natural teeth of the residual bite, a pattern of deflection of the jawbone-anchored unit or units which nicely approximates that of the natural teeth should be striven for. Probably, this will result in a considerably more favorable stress distribution throughout both the jawbone-anchored fixtures and across the superstructure/bridge construction which is connected between the fixture and the natural teeth.

Even in those cases where a bridge construction is anchored in the jawbone of a completely edentulous jaw, there may be a need to increase the patient's oral comfort by means of a gentler, less inflexible occlusion realized by means of an elastic element.

Also in extra-oral prostheses, for example joint prostheses, there is a need in this Art for a more elastic suspension of the prostheses in order to increase the feeling of comfort and, above all, to provide for a greater degree of inherent margin to destructive energy transmission level in that the elastic suspension, by deflection, on the one hand automatically leads to less force absorption over the region of the prosthesis and, instead, greater force is absorbed by, for example, the natural extremities, and, on the other hand considerably retards the velocity of the applied force. The possibility of elastic deflection also increases the time margin for the onset of the reflex protective reactions of the organism.

SUMMARY OF THE INVENTION

Hence, the object of the present invention is to provide a connecting device which, on the one hand, reduces the velocity of force on its application and, on the other hand, contributes to a more favorable distribution of applied forces and stresses on the bone-anchored prosthesis and natural, force-absorbing structures. According to the invention the connecting device comprises a cap-shaped matrix whose base is disposed to be connected to the fixture by the intermediary of an extant spacer, and the matrix also includes a resilient portion by the intermediary of which the matrix is connected to the outer prosthesis portion, such that this will be elastically anchored to the matrix.

In one preferred embodiment of the present invention, the connecting device further includes an outer, sleeve-shaped patrix connected to the outer prosthesis portion, for example by casting, the resilient portion consisting of a separate member interposed between an outer abutment on the matrix and a corresponding inner annular heel on the patrix.

In such an instance, the annular heel of the patrix may suitably be caused to cooperate with the abutment on the matrix such that an annular tunnel of substantially rectangular cross-section will be formed for the resilient member. This advantageously includes an O-ring of rubber, but may also comprise suitable metal material.

In one alternative embodiment of the present invention, the resilient member constitutes an integral part of the matrix, formed, for example, by an excision of the material of the matrix, the matrix including an exterior thread for, connection to the outer prosthesis portion, either directly or through an outer, sleeve-shaped patrix provided with a corresponding inner thread. The entire mounting cap may, in such instance, suitably be made of plastic or appropriate rubber material, such as, for example, EPDM (ethylene-propylene) rubber.

BRIEF DESCRIPTION OF THE DRAWINGS

The nature of the present invention and its aspects will be more readily understood from the following brief description of the accompanying Drawings, which show a number of examples of how the connecting device may be designed, and discussion relating thereto.

In the accompanying Drawings.

DESCRIPTION OF PREFERRED EMBODIMENTS

The connecting devices are advantageously designed for connection to existing standardized parts. Hereby, the connecting devices may be utilized both for individual jawbone-anchored crowns in residual bite with or without connection to the patient's own teeth, and for bridge constructions with or without residual bite connection.

Figure 1:
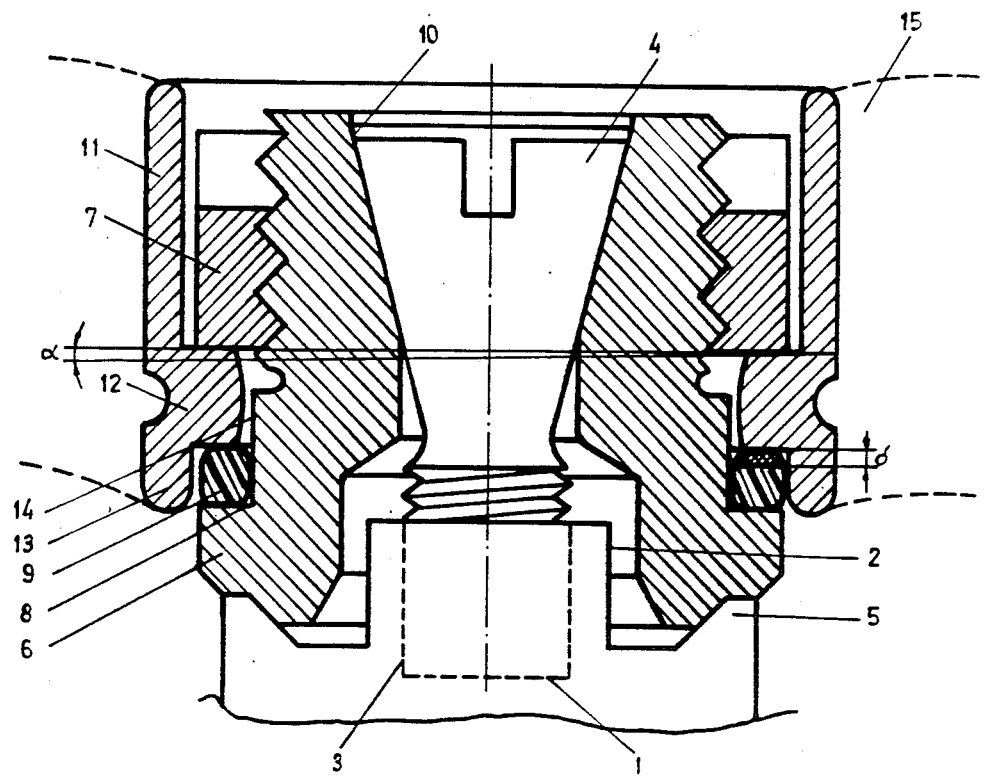
FIG. 1 shows a first embodiment with separate resilient member.

Referring now to the Drawings, FIG. 1 shows the upper portion of a spacer 1 which is disposed on a fixture (not shown) implanted in the jawbone tissue. The spacer 1 is provided with a central, cylindrical spacer screw 2 with a threaded bore 3 for a locking screw 4. The spacer 1 is provided with a collar 5 which, in the extant systems, forms a substrate for the mounting cap (matrix) 6 which, in turn, is united with that crown or bridge construction which is to be set in place.

The locking screw 4 is provided with a conical, downwardly tapering surface for fixedly locking the cap. Both the spacer 1 and the locking screw 4 are previously known in the art components and will not, therefore, be described in greater detail.

The connecting device according to the present invention comprises the cap-shaped matrix 6, for example of dental gold, titanium or plastic. Its base connects to the spacer 1 in the same manner as does the cap in the extant system. However, the matrix now under consideration is provided with an exterior thread arrangement (M4×0.5) for a ring nut 7. The matrix is further provided with an abutment or shelf 8 adapted to the resilient member in the form of, for example, an O-ring 9 of high-quality rubber.

The matrix has a conical through-passage 10 which communicates with the conical surface of the locking screw. The locking screw 4 rigidly draws the cap-shaped matrix 6 fast in place in the same manner as is previously known for fixedly locking the mounting cap.

The O-ring 9 consists of high-quality rubber, for example EPDM (ethylene-propylene) rubber and, is dimensioned to permit a downward deflection of the order of magnitude of $\alpha = 100-200$ μm in this case. In eccentric oblique loading, this corresponds to a maximum angular displacement $\alpha$ of 1°–2°, which must be considered as fully satisfactory in view of possible connection to natural teeth.

The connecting device further includes a sleeve-shaped patrix 11, for example of titanium, plastic or gold, fitted with a heel 12 which depresses the O-ring 9, and a portion 13 running at right angles to the heel 12 and enclosing, together with the heel 12, the matrix abutment or shelf 8 and the matrix wall 14, the O-ring 9 in a round tunnel of rectangular cross-section. In the production of the crown or bridge construction, respectively, the patrix 11 is cast or fixed by other means in the crown/bridge 15 which, through this patrix, will be elastically anchored to the matrix—the locking screw—the spacer.

This resilient anchorage is locked by means of the ring nut 7, also manufactured of, for example, gold. The ring nut 7 is threaded down to a light pre-tensioning of the O-ring, marked by a groove in the upper edge of the nut which must then register with a corresponding groove marking in the upper edge of the matrix. By a further two such markings in the matrix edge, to which the nut marking may be advanced, both moderate and hard pre-tensioning of the connecting device are permitted. The upper surface of the connecting device may be covered with, for example, a gold washer, once the nut 7 and the locking screw 4 have been locked by a droplet of acrylate. Acrylate is applied over the gold washer in order to fill the aperture in the crown/bridge construction through which the locking screw and the ring nut have been sited in place.

Figure 2:
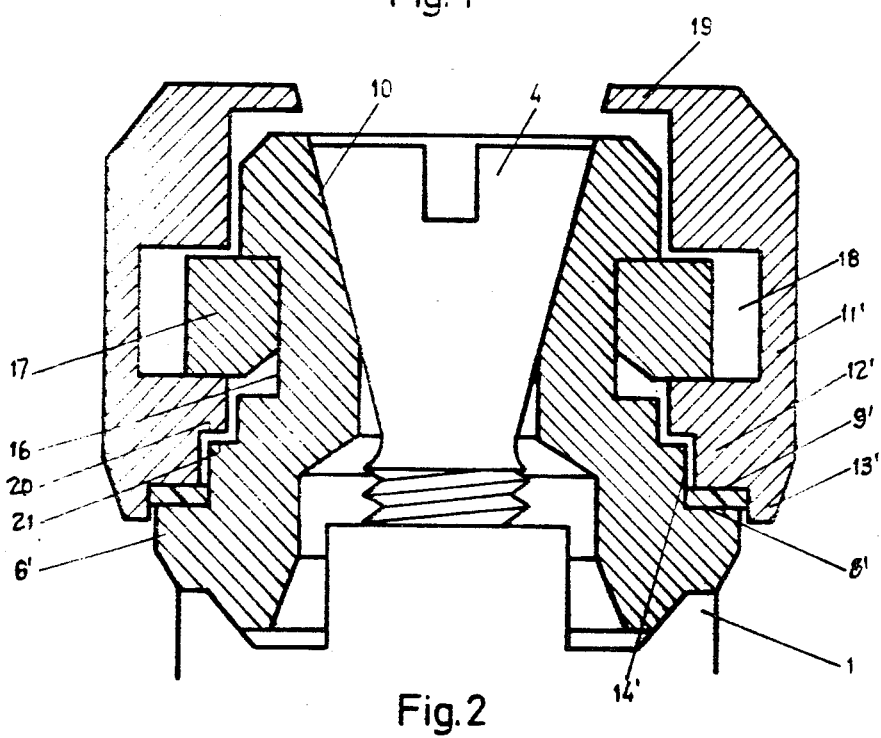
FIG. 2 shows a first variation of the embodiment of FIG. 1.

FIG. 2 illustrates an alternative embodiment of the connecting device of the present invention. Also in this case, the connecting device is coupled to prior Art extant spacer 1 by a locking screw 4. The connecting device includes a cap-shaped matrix 6' whose base connects to the spacer 1 in the same manner as in the foregoing embodiment. The matrix 6' is similarly provided with a conical through passage 10 which communicates with the conical surface of the locking screw 4. The matrix 6' is also provided with an abutment or shelf 8 adapted to a resilient element in the form of an O-ring 9' of high-quality rubber.

Also in this embodiment, the connecting device includes a sleeve-shaped patrix 11', of titanium, plastic or gold, fitted with a heel 12' which depresses the O-ring 9', and a portion 13' running at right angles to the heel 12' and enclosing, together with the heel 12', the matrix abutment or shelf 8' and the matrix wall 14', the O-ring 9' in a round tunnel of rectangular cross-section.

The connecting device according to this embodiment differs in the design of the locking arrangement and the patrix 11'. Instead of an outer thread and ring nut, the matrix is provided with a circular outer recess 16 for a locking washer 17 of plastic, for example, Peek 450 (R), which abuts against the heel 12' of the patrix 11' by a recess 18 in order to make for light pre-tensioning of the O-ring.

The upper portion of the patrix is provided with an annular flange 19 which extends in over the end portion of the matrix and thereby results in a considerably smaller aperture in the crown/bridge construction than is the case in the first embodiment. Furthermore, the lower portion of the patrix may be provided with a further, inner heel 20 which, in the event of overload, cooperates with a corresponding matrix shelf 21 and thereby prevents puncture of the O-ring 9'.

Bench tests of prototypes of the connecting device with the above-disclosed components have shown that the deflection pattern fundamentally agrees with the deflection of, for example, a tooth, in other words such deflection is initially relatively great in relation to the applied force and logarithmically reduces on constant force increase. By governing the pre-tension of the connecting device, it is possible to determine at which level of force or at which moment of forces measurable deflection is to occur.

Figure 3:
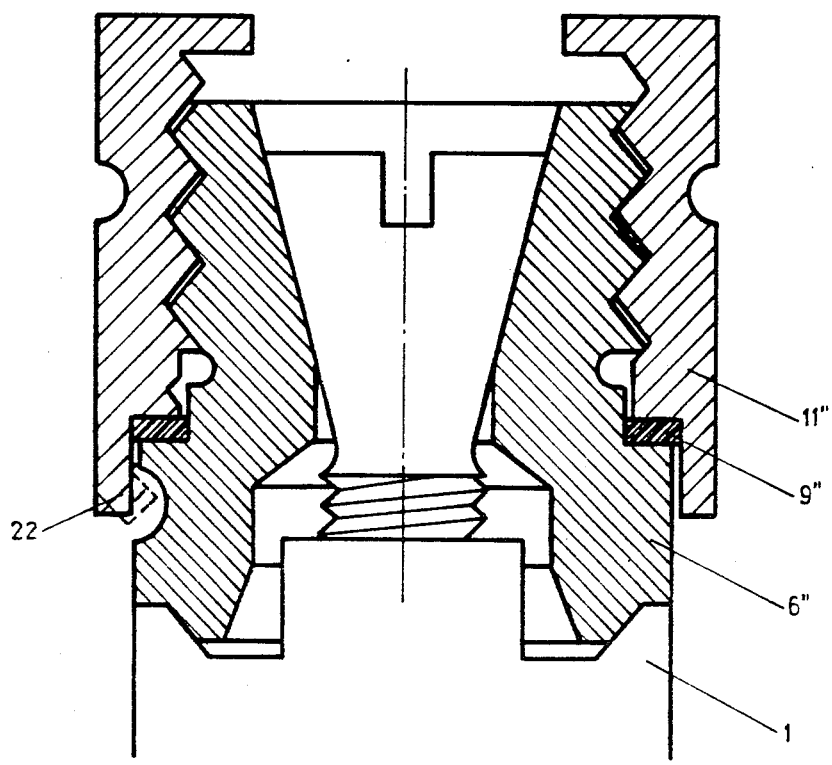
FIG. 3 shows a second variation of the embodiment of FIG. 1.

FIG. 3 shows yet a further embodiment exemplifying how the connecting device may be designed. Also in this embodiment, the connecting device comprises a cap-shaped matrix 6", whose base connects to the spacer 1, and a patrix 11' cast in the crown/bridge construction. An O-ring 9" of high-quality rubber is enclosed in a round tunnel of rectangular cross-section in a manner similar to that in the two preceding embodiments.

The matrix 6" is provided with an outer thread arrangement and, in this case, is directly threaded into the patrix 11'. In such instance, the thread arrangement has a degree of play which permits a certain deflection of the patrix in relation to the matrix, for example of the order of magnitude of 50 μm. This deflection will, here, be "counter-balanced" by the O-ring 9" in the same manner as in the earlier embodiments.

The advantage inherent in this embodiment is that no locking nut or overload guard in the form of cooperating surfaces 20, 21 (see FIG. 2) will be required. The necessary locking may, here, readily be realized by a burring 22. Moreover, the aperture in the crown or bridge construction may be made as small as the head of the locking screw, for example as small as in standard construction.

Figure 4:
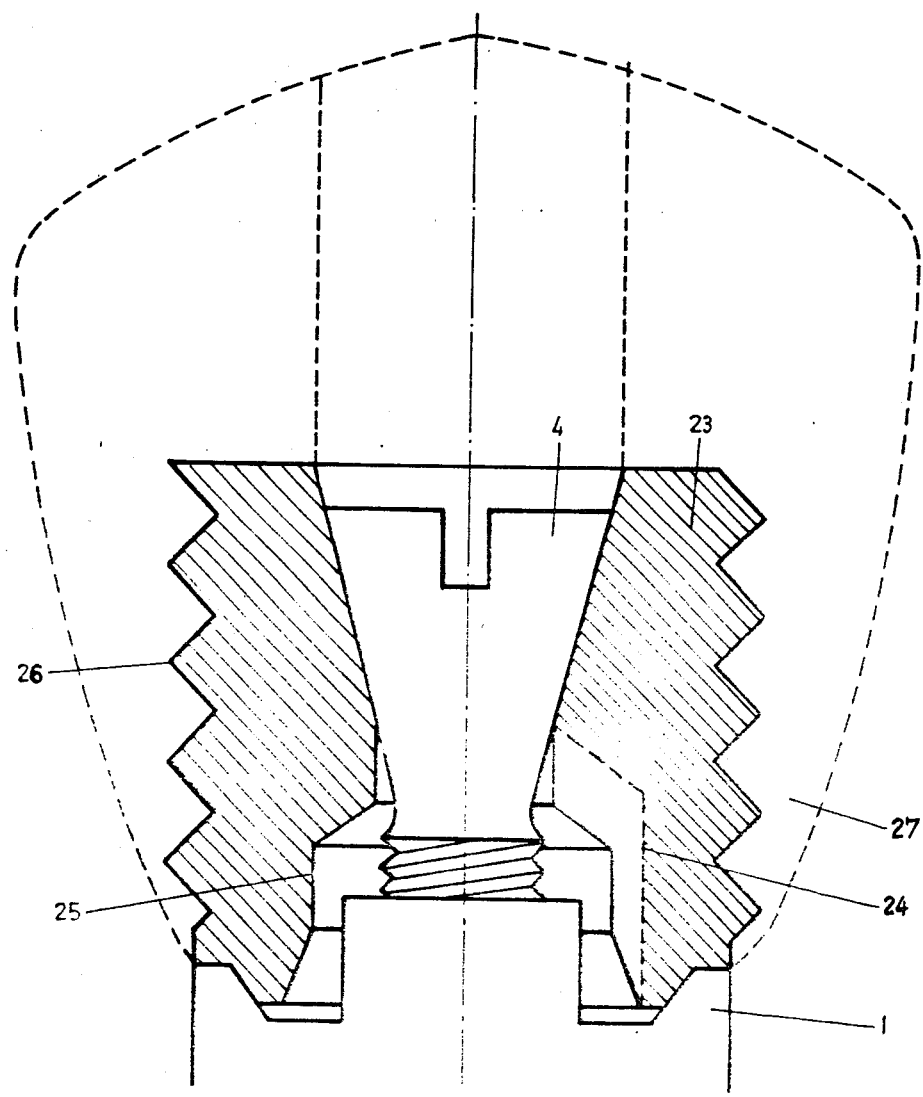
FIGS. 4 and 5 show examples of alternative embodiments of the present invention in which the resilient member consists of an integrated part of the matrix.

FIG. 4 shows an alternative embodiment in which the connecting device consists of a cap-shaped matrix 23 made entirely of plastic or suitable rubber, for example EPDM (ethylene-propylene) rubber. The base of the matrix connects to an extant spacer 1 in the same manner as in the first embodiment and, further, is provided with a conical surface which connects with the conical surface of the locking screw 4. However, the matrix 23 is made of such material as to become rigidly anchored by the locking screw 4 in its upper portion, at the same time as its lower portion, by means of suitably adapted excision 24, 25, yields up to 100–200 μm on loading.

The yielding mounting cap 23 is provided with an outer thread 26 and is screwed in place in a corresponding inner thread in a patrix or directly into a single crown or bridge construction 27. As a result, the aperture in the crown or bridge construction may be made as small as the head of the locking screw 4, for example as small as in standard construction.

Figure 5:
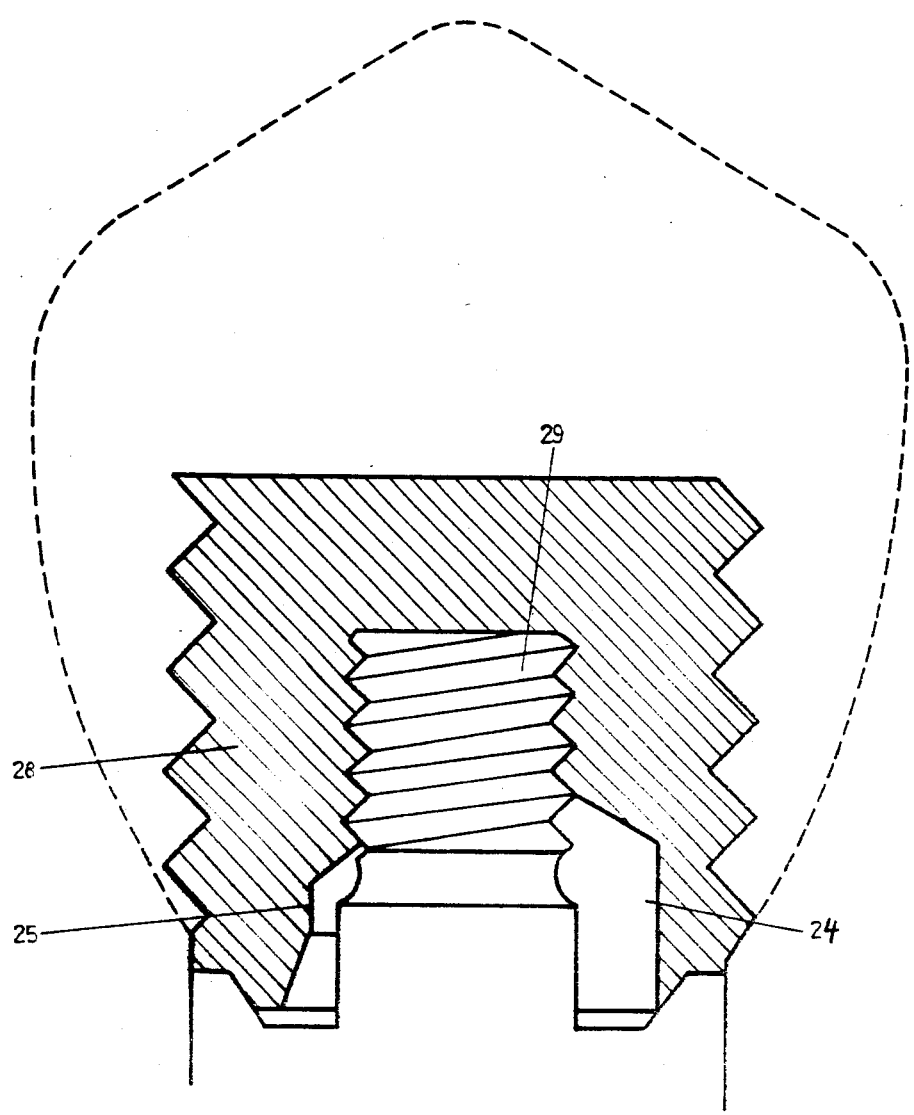

FIG. 5 shows a variation in which the entire single crown is made of hard rubber or yielding plastic, the cervical core 28 of the crown most proximal the spacer being that portion which yields most. This may be realized in that the above-described mounting cap is polymerized together with an individually produced plastic crown. In this case, the spacer 1 is provided with a central, cylindrical spacer screw with an extended, exteriorly threaded pin 29.

This latter variation may be appropriate in the event of problems relating to shortage of space or aesthetic difficulties, since advantages are to be gained in that the individual crown is screwed onto the pin 29. The core of the crown will then consist of a both internally and exteriorly threaded mounting cap of suitably resilient material which is applied from beneath and is locked by a "snap action" against both the exteriorly threaded pin 29 and the crown. In this case, the separate locking screw and the aperture in the crown may be dispensed with.

The present invention should not be considered as restricted to that described above and shown on the Drawings, many modifications being conceivable without departing from the spirit and scope of the appended Claims.

What we claim and desire to secure by Letters Patent is:

1. A connecting device for dental prosthesis for connecting a first portion of a prosthesis partially implanted into body tissue to a second peri-tissual outer portion of the prosthesis, the first portion including an anchorage unit for implantation into tissue and a spacer having a lower collar-shaped part disposed on the anchorage unit and a screw member extending upwardly from the lower part, the lower collar-shaped part having a top surface including a horizontal portion and an inclined portion, said connecting device comprising:

a cap-shaped member (6) having a base portion for connection to the lower collar-shaped part of the spacer, said base portion having a bottom surface corresponding to the top surface of said collar-shaped part, said base portion being provided with an outwardly extending annular abutment (8);

a first locking means (4) for interlocking said cap-shaped member to said spacer;

an outer sleeve-shaped member (11) having an external surface for connection to the outer prosthesis portion, said outer member being insertable over said cap-shaped member and having a base portion including a corresponding annular heel, said annular abutment and said heel forming a space therebetween;

a resilient member (9) disposed in said space and elastically connecting said cap-shaped member to said outer member, whereby a favorable stress distribution is provided between implanted and peri-tissual outer prosthesis portion; and, a second locking means (7) for locking said outer sleeve-shaped member to said cap-shaped member.

2. The connecting device according to claim 1 wherein said annular heel (12, 12') of said outer sleeve member (11, 11', 11") cooperating with said abutment (8, 8') of said cap-shaped member (6, 6', 6") form an annular tunnel of substantially rectangular cross-section for receiving said resilient member (9, 9', 9").

3. The connecting device according to claim 2 wherein said resilient member (9, 9', 9") forms an O-ring member.

4. The connecting device according to claim 3 wherein said O-ring is made of high-quality rubber.

5. The connecting device according to claim 3 wherein said O-ring is made of ethylene-propylene rubber.

6. The connecting device according to claim 3 wherein said O-ring member has a thickness of about 0.5 mm.

7. The connecting device according to claim 1 wherein said resilient member (9, 9', 9") comprises a resilient metal washer.

8. The connecting device according to claim 1 wherein said second locking means includes a ring nut (7) connectable to an outer thread of said cap-shaped member (6) for abutment against said annular heel (12) of said outer member (11) for imparting a pre-tensioning to said resilient member (9).

9. The connecting device according to claim 1 wherein said second locking means is a locking washer (17) disposed in an external recess (16) of said cap-shaped member (6) for abutment against said annular heel (12) of said outer member (11) for imparting a pre-tensioning to said resilient member (9).

10. The connecting device according to claim 9 wherein the upper portion of said outer member (11) is provided with an annular flange (19) extending inwardly over the top end portion of said cap-shaped member (6').

11. The connecting device according to claim 1 wherein said cap-shaped member (6") is connected to said outer sleeve (11") by an exterior thread arrangement, with a play which permits some deflection of said outer sleeve with respect to said cap-shaped member.

* * * * *